April 6, 1971 S. J. BORSH Plant Pat. 3,039
CHRYSANTHEMUM
Filed Jan. 3, 1969
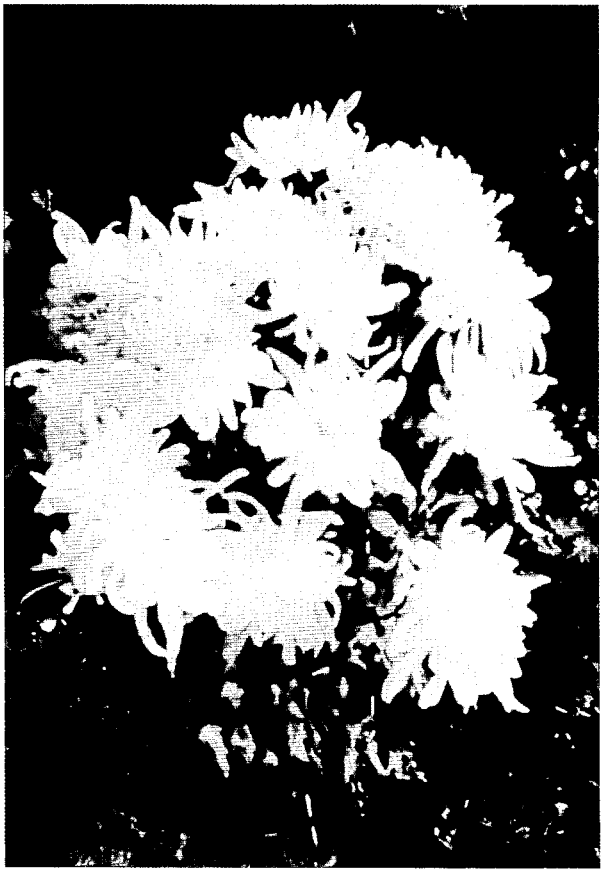

United States Patent Office

Plant Pat. 3,039
Patented Apr. 6, 1971

3,039

CHRYSANTHEMUM

Steven J. Borsh, North Hollywood, Calif.
(4547½ Auhay Drive, Santa Barbara, Calif. 93105)

Filed Jan. 3, 1969, Ser. No. 788,968
Int. Cl. A01h *5/00*
U.S. Cl. Plt.—78 1 Claim

This invention relates to a new and distinct variety of chrysanthemum plant characterized by it floriferrousness, large blossom size and compact growth habit.

My new plant was first discovered as a seedling in a planting of chrysanthemums derived from a mutation of an unknown variety. The latter plant was approximately four and one half feet in height and bore 3" blooms. The mutation was generally similar to its parent plant, but bore 6" blooms. The instant variety was selected for propagation and further observation since it retained the 6" blossom size but had a neater, more compact growth habit. I have propagated my new variety by cuttings, which propagations retain the characteristics of the original seedling.

*Detailed description*

Parentage: Unknown
Classification: Decorative

Height: 26 inches without pinching
Blooming period October 15 in Santa Barbara, Calif.
Blossom:
*Size.*—5–7 inches.
*Stem.*—Wiry, erect, few side buds.
*Form.*—Decorative, peony, high-crested.
*Color.*—Creamy yellow center shading to almost pure white outer petals.
*Petals.*—Texture—good, long lasting.

*Plant*

Form: Upright, compact, generally not branching.
Growth: Sturdy, wiry.
Foliage: Deep green, abundant, crinkled, average texture.
Hardiness: Unknown.

I claim:

1. A new variety of chrysanthemum plant substantially as shown and described, characterized by a peony-form blossom and compact growth.

No references cited.

ROBERT E. BAGWILL, Primary Examiner